United States Patent
Hoganson et al.

(10) Patent No.: US 10,670,585 B2
(45) Date of Patent: Jun. 2, 2020

(54) SYSTEM AND METHOD FOR IN VITRO BLOOD VESSEL MODELING

(71) Applicants: David M. Hoganson, Boston, MA (US); Joseph P. Vacanti, Winchester, MA (US); Jeffrey T. Borenstein, Newton, MA (US)

(72) Inventors: David M. Hoganson, Boston, MA (US); Joseph P. Vacanti, Winchester, MA (US); Jeffrey T. Borenstein, Newton, MA (US)

( * ) Notice: Subject to any disclaimer, the term of this patent is extended or adjusted under 35 U.S.C. 154(b) by 576 days.

(21) Appl. No.: 15/440,888

(22) Filed: Feb. 23, 2017

(65) Prior Publication Data

US 2017/0241991 A1    Aug. 24, 2017

Related U.S. Application Data

(62) Division of application No. 12/866,968, filed as application No. PCT/US2009/033736 on Feb. 11, 2009, now Pat. No. 9,595,206.

(60) Provisional application No. 61/065,356, filed on Feb. 11, 2008, provisional application No. 61/103,117, filed on Oct. 6, 2008.

(51) Int. Cl.

| | |
|---|---|
| *G01N 33/50* | (2006.01) |
| *A61L 27/18* | (2006.01) |
| *A61L 27/38* | (2006.01) |
| *A61L 27/50* | (2006.01) |
| *A61L 27/56* | (2006.01) |
| *C12M 3/00* | (2006.01) |
| *C12M 1/12* | (2006.01) |
| *C12M 1/42* | (2006.01) |
| *C12M 1/00* | (2006.01) |
| *G09B 23/28* | (2006.01) |
| *B01L 3/00* | (2006.01) |

(52) U.S. Cl.
CPC .......... *G01N 33/5088* (2013.01); *A61L 27/18* (2013.01); *A61L 27/38* (2013.01); *A61L 27/507* (2013.01); *A61L 27/56* (2013.01); *B01L 3/502707* (2013.01); *C12M 21/08* (2013.01); *C12M 23/34* (2013.01); *C12M 25/02* (2013.01); *C12M 35/08* (2013.01); *G09B 23/28* (2013.01); *B01L 3/5027* (2013.01); *B01L 2200/027* (2013.01); *B01L 2300/0681* (2013.01)

(58) Field of Classification Search
CPC .......................... G01N 33/5088; A61L 27/18
See application file for complete search history.

(56) References Cited

U.S. PATENT DOCUMENTS

| | | | | |
|---|---|---|---|---|
| 2005/0202557 A1* | 9/2005 | Borenstein | .......... | A61M 1/1678 |
| | | | | 435/369 |
| 2009/0053752 A1* | 2/2009 | Blackman | ............ | C12N 5/0691 |
| | | | | 435/29 |

FOREIGN PATENT DOCUMENTS

WO    WO2008127732    * 10/2008    ............... A61F 2/02

OTHER PUBLICATIONS

Louden et al., Biomarkers and Mechanisms of Drug-induced vascular injury in non-rodents, Toxicologic Pathology, vol. 34, p. 19-26. (Year: 2006).*

* cited by examiner

*Primary Examiner* — Taeyoon Kim
*Assistant Examiner* — Tiffany M Gough
(74) *Attorney, Agent, or Firm* — Adler Pollock & Sheehan P.C.

(57) ABSTRACT

The present invention provides an in vitro blood vessel model for investigation of drug induced vascular injury and other vascular pathologies. The in vitro blood vessel model provides two channels separated by a porous membrane that is coated on one side by an endothelial cell layer and is coated on the other side by a smooth muscle cell layer, wherein said model is susceptible to the extravasation of red blood cells across said porous membrane due to drug induced vascular injury.

6 Claims, 6 Drawing Sheets

SYSTEM AND METHOD FOR IN VITRO BLOOD VESSEL MODELING

CROSS-REFERENCE TO RELATED APPLICATIONS

Related Applications

This application is a Divisional Application of U.S. patent application Ser. No.: 12/866,968 filed on Oct. 21, 2010, which is the U.S. national phase, pursuant to 35 U.S.C. § 371, of PCT International Application No. PCT/US2009/033736, filed Feb. 11, 2009, which claims the benefit of U.S. Provisional Application 61/065,356, filed Feb. 11, 2008, and U.S. Provisional Application 61/103,117, filed Oct. 6, 2008. The entire contents of the aforementioned patent applications are incorporated herein by this reference.

FIELD OF THE INVENTION

The present invention relates to a system and method for creating an in vitro blood vessel model to investigate drug induced vascular injury and other vascular pathology.

BACKGROUND OF THE INVENTION

Blood vessels are a tissue central to many disease states. One such disease state is drug induced vascular injury (DIVI), a pathological insult to blood vessels that occurs after the administration of a drug. DIVI causes smooth muscle cell (SMC) death and hemorrhage and is characterized by the extravasation of red blood cells (RBCs) from the vascular lumen into surrounding SMC layers. This phenomenon occurs without overt damage to the endothelial cells (ECs). The cause of DIVI is poorly understood but its occurrence often halts in vivo testing of candidate drugs.

The predilection for DIVI is unclear. The central and only specific event in DIVI is the extravasation of RBCs into the media of the effected blood vessels. Currently, the molecular mechanisms of DIVI are unclear and no specific biomarkers are known that allow DIVI to be distinguished from other forms of vascular injury. It is contemplated that improved understanding of the mechanisms of DIVI will improve the screening of drugs under development and better correlate the significance of in vivo animal testing and human susceptibility to DIVI.

It would therefore be desirable to develop an in vitro model of a small diameter blood vessel to allow the study of a variety of vascular diseases and physiological mechanisms. In particular, the model would be used to investigate the mechanisms and biomarkers of DIVI in animals and humans. It would provide a platform for the screening of drugs under development and allow disease processes effecting small to medium sized vessels to be investigated.

SUMMARY OF THE INVENTION

In a first aspect the present invention provides an in vitro blood vessel model comprising two channels separated by a porous membrane that is covered on one side by endothelial cells and is covered on the other side by smooth muscle cells, wherein said model is susceptible to the extravasation of red blood cells across said porous membrane due to drug induced vascular injury.

The porous membrane may be designed to mimic the internal elastic lamina of blood vessels, preferably having a porosity of approximately 11%, pore sizes ranging from 2.3-13 µm, and an average pore size of 6.4 µm. It is contemplated that this porous membrane is a track-etched polycarbonate membrane that may be coated with at least one of elastin, fibrinogen, and collagen, or combinations thereof.

The in vitro blood vessel model includes a luminal channel designed to mimic the lumen of a small blood vessel and a smooth muscle channel designed to mimic the medial layer of a blood vessel. It is also contemplated that, in the preferred embodiment, the smooth muscle channel is an open smooth muscle channel that may be capped by a lid and may include beveled walls adjacent to the porous membrane.

In a certain embodiment of the present invention, the in vitro blood vessel model includes smooth muscle and luminal channels having offset inflow and outflow ponds that reduce non-physiological shear stress on the porous membrane.

In another aspect of the present invention, a method of assaying an agent for its ability to cause drug induced vascular injury is provided. Such a method comprises, providing an in vitro blood vessel model comprising two channels separated by a porous membrane that is coated on one side by an endothelial cell layer and is coated on the other side by a smooth muscle cell layer, wherein said model is susceptible to the extravasation of red blood cells through said porous membrane due to drug induced vascular injury, passing the agent through the channel adjacent the endothelial cells of the in vitro model, and analyzing the channel adjacent the smooth muscle cells for the extravasation of red bloods cells, which indicates that the agent causes drug induced vascular injury.

These and other features, objects and advantages of the present invention will become better understood from the description that follows. The description of preferred embodiments is not intended to limit the invention to cover all modifications, equivalents and alternatives. Reference should therefore be made to the claims recited herein for interpreting the scope of the invention.

DESCRIPTION OF THE PREFERRED EMBODIMENTS

The present invention provides an in vitro model of a blood vessel, through which blood or culture media flows at physiological rates, that allows the investigation of a variety of vascular diseases and physiological mechanisms.

Figure 1:
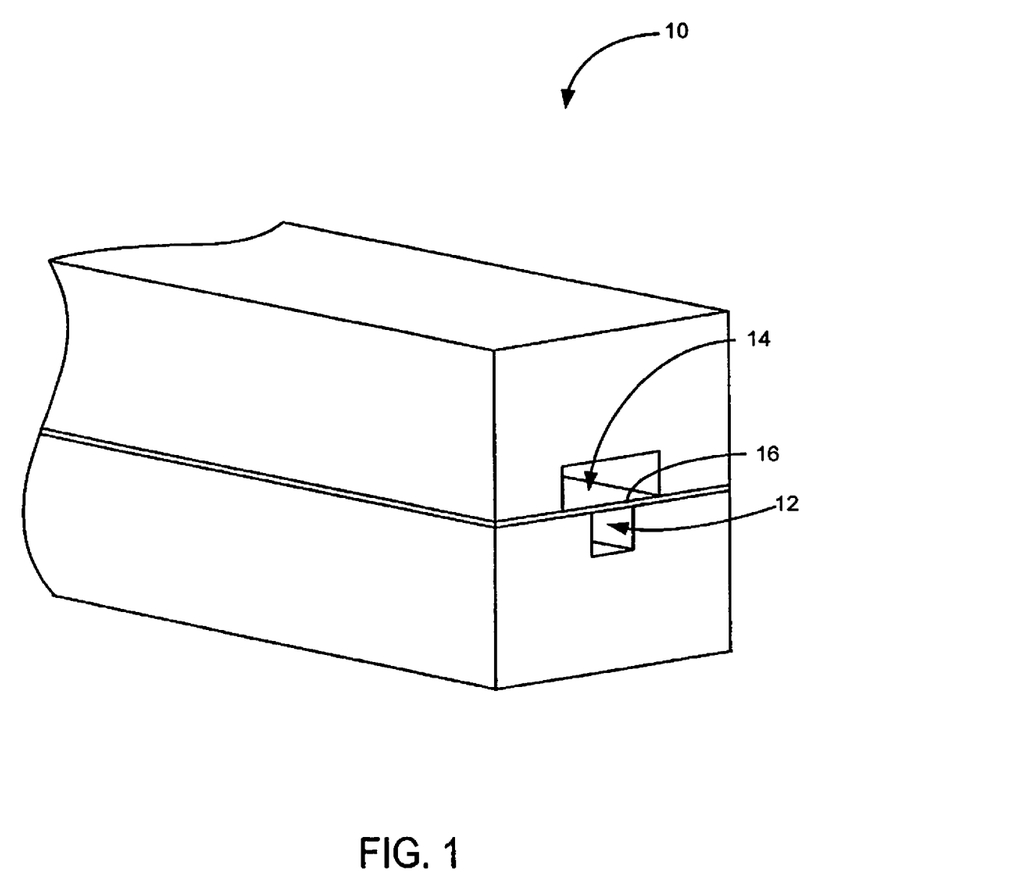
FIG. 1 shows a perspective view of a microfluidic device according to one embodiment of the present invention, including a closed smooth muscle channel.
Figure 2:
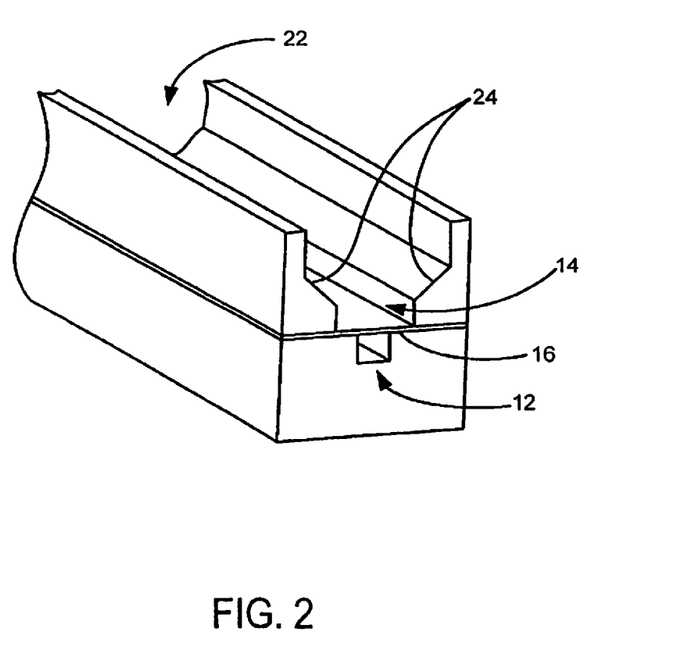
FIG. 2 shows a perspective view of a microfluidic device according to one embodiment of the present invention, including an open smooth muscle channel with beveled walls.

Referring to FIGS. 1-2, the present invention includes a microfluidic device 10 having a luminal channel 12 separated from a smooth muscle channel 14 by a porous membrane 16.

Figure 3A:
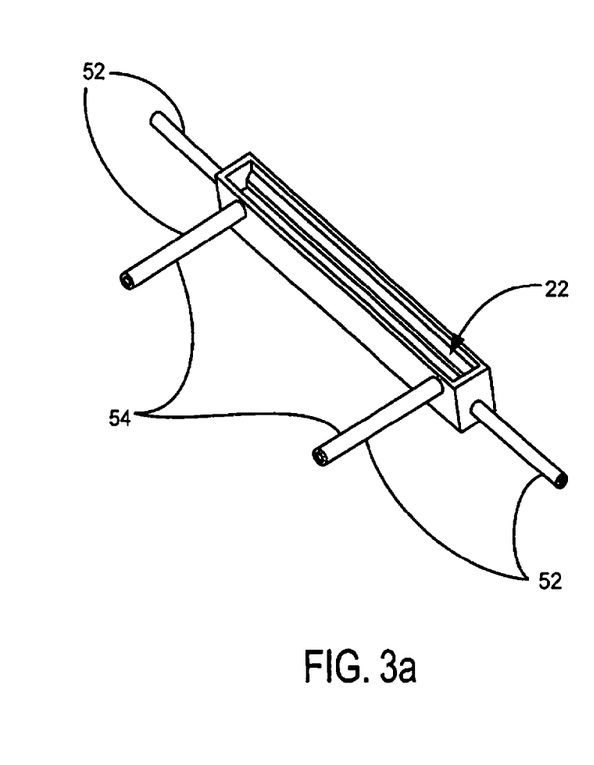
FIGS. 3a and 3b respectively show an open smooth muscle channel with and without a lid in accordance with one embodiment of the present invention.
Figure 3B:
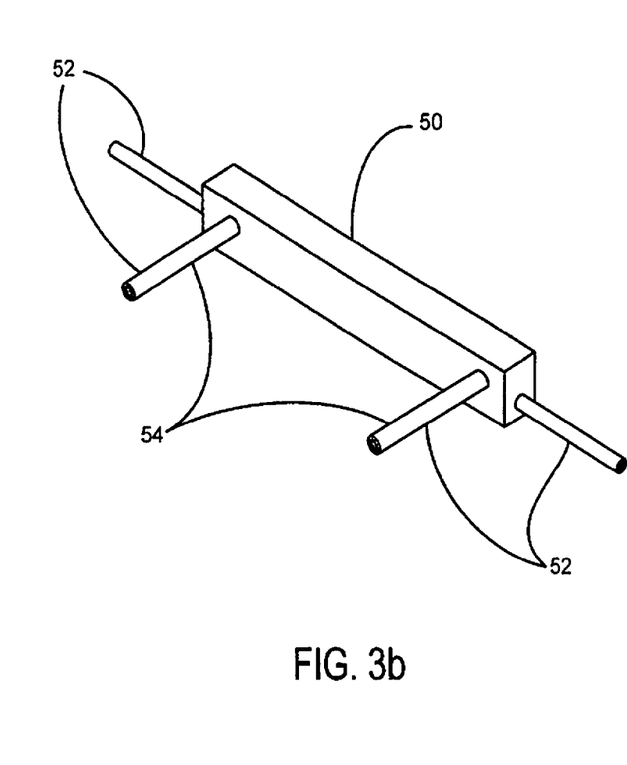

The luminal channel 12 models the lumen of a blood vessel and may also be referred to as the vascular channel or vascular lumen. The smooth muscle channel 14 is designed to allow SMC growth and models the medial layer of the blood vessel. It is contemplated that SMC growth may be better facilitated by employing an open smooth muscle channel 22, which provides access to increased volumes of growth media, and beveled sides 24, which allow cells to more readily come into contact with the membrane. This arrangement provides more uniform seeding of the device and minimizes the number of cells which attempt to attach to the non-membrane portion of the smooth muscle channel 14. Referring to FIG. 3, the open smooth muscle channel 22 may be capped with a lid 50 to create a large, media volume to promote SMC growth while improving usability and sterile culture conditions. The lid 50, which is shown removed in FIG. 3a and applied in FIG. 3b, can be applied before or after SMC seeding.

Figure 4:
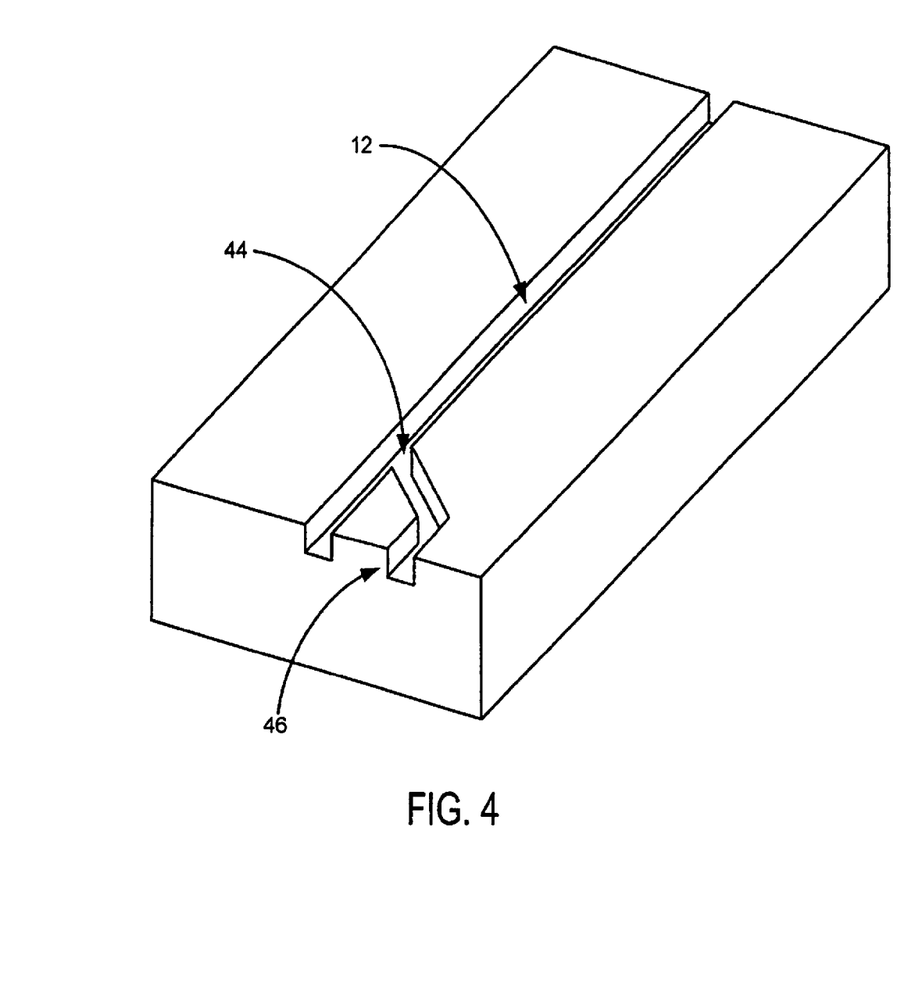
FIG. 4 shows a bifurcated luminal channel in accordance with one embodiment of the present invention.

Referring to FIGS. 1 and 4, it is contemplated that the vascular and smooth muscle channels, 12 and 14 respectively, have a round or hydraulic diameter of approximately 200 μm, as DIVI typically occurs in mesenteric vessels of this size. Other diameters are possible and the present invention may also include branching channels with single or multiple bifurcations. For example, the luminal channel 12 may include a bifurcation 44 providing a second access 46 that allows luminal channel access without disturbing any tubing connections used to establish to create flow. In such a configuration, media flows through the central, linear portion of the luminal channel 12 and mimics physiological shear stress within the blood vessel lumen. Cells for may then be seeded into the blood vessel lumen using the second access 46 and a fitting adapted for seeding cells without disturbing the central channel's flow connections. It is contemplated that the second access 46 can also be used to inject drugs or other reagents.

Referring again to FIG. 1, the luminal and smooth muscle channels are separated by a porous membrane 16 that approximates the internal elastic lamina of blood vessels. The internal elastic lamina is an extracellular matrix layer disposed between the endothelial cells of the intima and the smooth muscle cells of the media. It is contemplated that the porous membrane 16 is a track-etched polycarbonate membrane coated with at least one of elastin, fibronectin, fibrin, laminin, hyaluronic acid, and collagen. A preferred embodiment may have a porosity of approximately 11%, pore sizes ranging from 2.3-13 μm, and an average pore size of approximately 6.4 μm. However, a range of porosities between approximately 5 and 50% and a range of pore sizes between 0.1 and 30 μm are possible. Moreover, the variance in pore size can also range and, in some cases, may be reduced to negligible levels. SMCs are seeded upon the side of the porous membrane 16 that faces the smooth muscle channel 14 to create a SMC membrane layer. Following seeding of SMCs, ECs are seeded upon the luminal side of the porous membrane 16 and are grown into an EC membrane layer. It is contemplated that the portion of the porous membrane adjacent to the ECs may be coated with different combinations or concentrations of extracellular matrix proteins than the porous portion of the membrane adjacent to the endothelial cells.

Blood flow through the device 10 at physiological flow rates generates physiological shear stress and causes RBCs to extravasate through the porous membrane 16 if the membrane does not include endothelial or smooth muscle cell layers. However, when ECs and SMCs are grown on opposing sides of the membrane, culture media including RBC's or 6 μm microspheres (that is, RBC analogs) flow through the luminal channel 12, but do not extravasate through the porous membrane 16 into the smooth muscle channel 14. Any combination of drugs and hemodynamic models can be applied to this model to investigate the mechanisms and potential biomarkers of drug induced vascular injury.

In another embodiment, the present invention provides an in vitro blood vessel model having 0.5-10 μm thick porous membrane including one or more proteins such as collagen, elastin, fibrin, fibronectin, laminin, hylauronic acid. This membrane, is initially less porous than the internal elastic lamina of a blood vessel, but, over time, is broken down or remodeled by the endothelial and/or smooth muscle cells to produce a membrane containing physiological proteins that allows the extravasation of RBCs or RBC analogs under appropriate conditions. This advantageously allows the continued adhesion of ECs to the membrane under high shear stress conditions. The membrane may further include an electrospun material, for example, polycaprolactone, coated with extracellular matrix proteins such as collagen. Alternately, the present invention can include a porous collagen membrane that allows the extravasation of RBCs. This porous collagen membrane may be crosslinked and may resist significantly remodeling by the cells over the course of the culture or experiment.

Additional cells can be cultured within or on the SMCs to further study vascular physiology or pathological states that occur in blood vessels, such as atherosclerosis and inflammation. For example, fibroblasts may be seeded above SMCs to replicate an adventitial-like layer to the blood model. The fibroblasts can be seeded into the SMC channel shortly after the SMCs have been seeded or after several days of SMC culture. In addition, adipocytes can be seeded above the SMCs or following seeding with fibroblasts. The adipocytes, with or without additional fibroblasts, allow the establishment of perivascular fat tissue similar to an in vivo condition.

Figure 5:
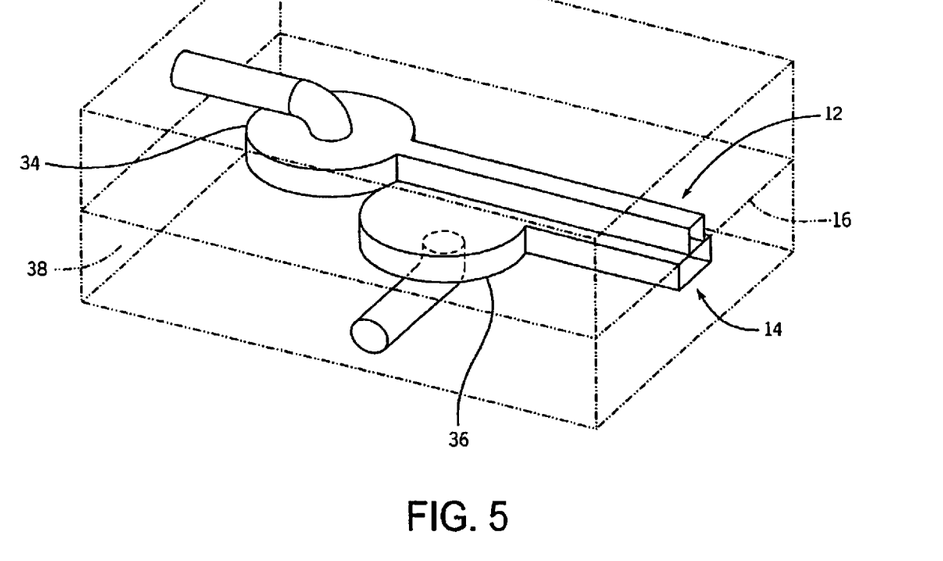
FIG. 5 shows one embodiment of the present invention, including offset ponds.

Referring now to FIG. 5, one embodiment of the microfluidic device 10 has inlet and outlet areas for the microfluidic channels that are known as ponds. Traditional microfluidic devices have overlapping ponds, but blood flow into overlapping ponds generates non-physiological shear stress on the porous membrane and a velocity vector directing fluid flow through the porous membrane. This arrangement can cause abnormal RBC extravasation and is not suitable for DIVI or vascular pathology testing, as it may obscure test results within the model. The present invention instead employs a vascular channel pond 34 offset from a smooth muscle channel pond 36. As a result, fluid force no longer causes RBC extravasation into the smooth muscle channel 14 at the pond, as the porous membrane 16 over the vascular channel pond 34 abuts a solid material.

Referring again to FIG. 3, one embodiment of the present invention includes tubes 52 that provide fluid access to the endothelial and smooth muscle channels. The tubes in communication with the smooth muscle channel 54 allow media change and at least one of the tubes may be connected to a sterile filter (for example, a syringe filter) and elevated to create an atmospheric pressure vent.

Figure 6:
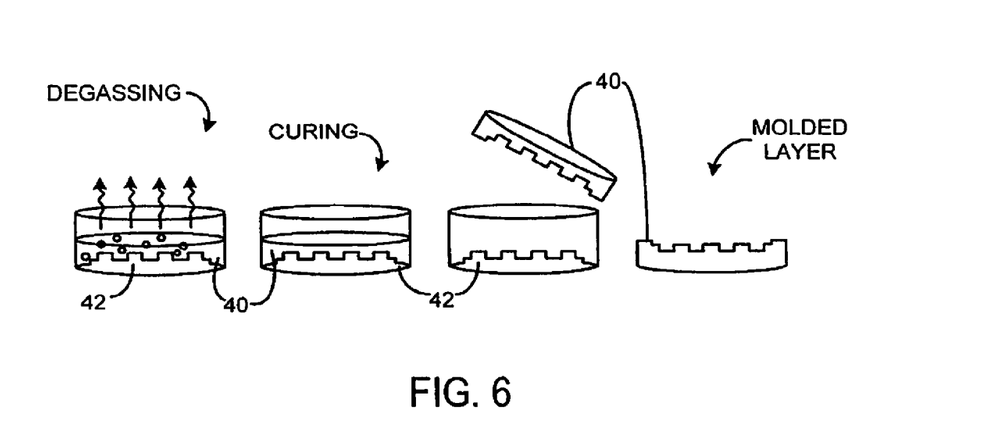
FIG. 6 shows a process that may be used to manufacture the present invention.

Referring to FIG. 6, it is contemplated that the microfluidic device is made from polydimethylsiloxane (PDMS) using soft photolithography techniques. This process includes creating two layers with half-depth channels 40 using a positive mold 42. Round or rectangular channels are made using a rectangular or half-round shaped mold, respectively.

In another embodiment, the microfluidic device may be placed in a single pass or recirculating system where culture media is passed through the device. The system determines and adjusts flow, overall pressure, and pressure waveform at the inlet and outlet of the device to produce a desired set of conditions, for example, physiologic conditions or pathological conditions observed in DIVI. These hemodynamic conditions, in addition to the presence or absence of a drug, may lead to an improved understanding of the mechanisms of DIVI.

Figure 7:
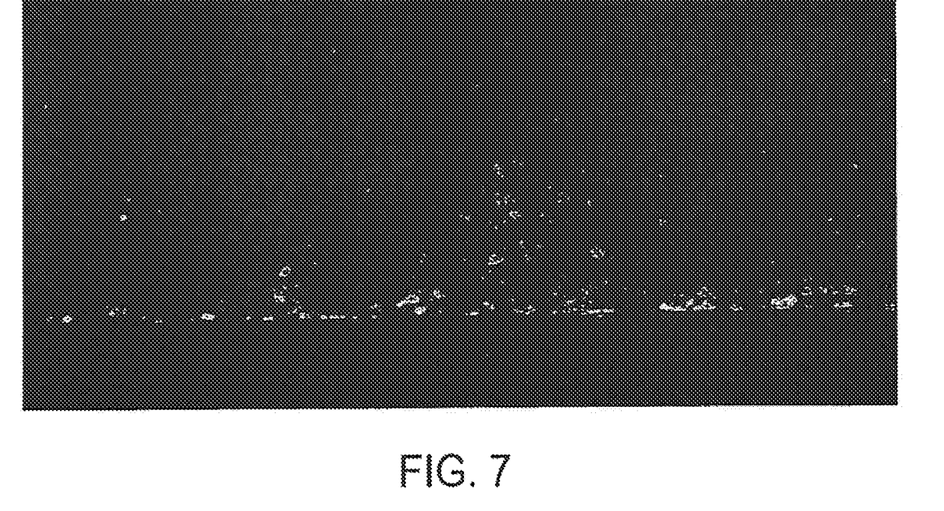
FIG. 7 shows an immunohistochemistry stain of F-actin on smooth muscle cells grown in an in vitro blood vessel model in accordance with the present invention.
Figure 8:
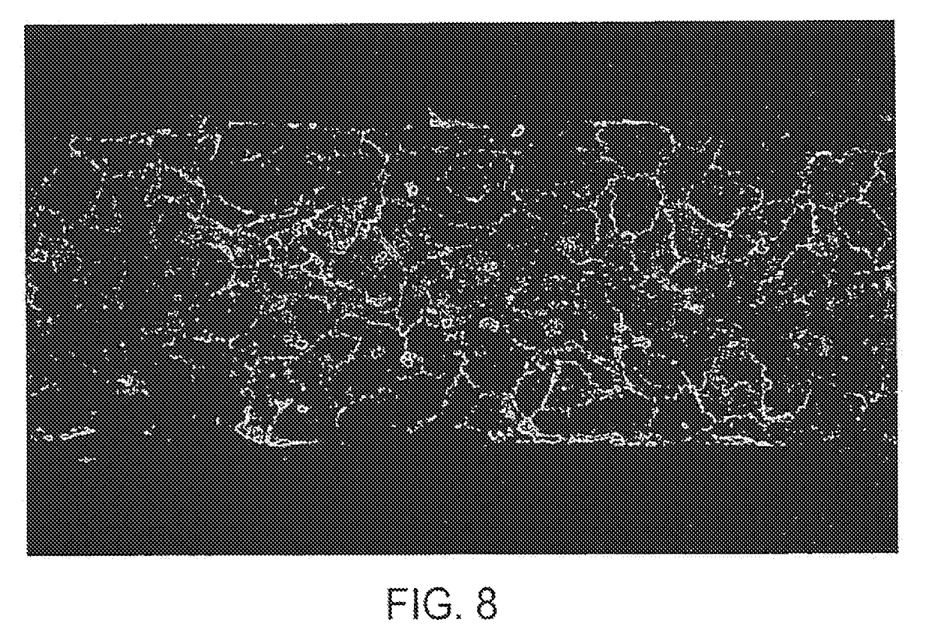
FIG. 8 shows an immunohistochemistry stain of CD31 and DAPI on endothelial cells grown in an in vitro blood vessel model in accordance with the present invention.

Referring to FIGS. 7 and 8, an in vitro blood vessel model in accordance with the present invention was used to study extravasation. This model included bifurcated inlets and a track-etched polycarbonate membrane having 10 µm pores. To study extravasation, both sides of the membrane were coated with type I rat tail collagen and primary rat aortic SMCs were then seeded within the open smooth muscle channel, attaching to the exposed membrane, but not attaching the PDMS regions. Following SMC seeding, a lid was applied to the top of the device to seal the SMC channel and a syringe filter was attached to the outlet tubing to vent the SMC channel to the atmosphere. As shown in FIG. 7, the SMCs were then stained with phalloidin for F-actin to demonstrate initial SMC coverage. After four days of SMC culture, dTomata-labeled primary rat aortic ECs were seeded into a 200 µm luminal channel and, four hours after EC seeding, flow with the 200 µm luminal channel was initiated using a syringe pump. Over the next seven days flow was increased to arterial flow rates, that is, approximately 15 dynes/cm$^2$ or 7200 µm/hr. Confluency of the cell layers was then demonstrated by flowing 6 µm diameter fluorescent microspheres through the device and evaluating bead extravasation into the smooth muscle layer or channel. The ECs and SMCs were the fixed and stained for CD31 and F-actin respectively.

The dTomato-labeled ECs indicated that the ECs formed a monolayer on the polycarbonate membrane within the luminal channel channel. This was further demonstrated by subsequent CD31 and DAPI (4',6-diamidino-2-phenylindole) staining, as shown in FIG. 8. This test demonstrated cell layer confluence and the physiological robustness of the model, as no extravasation of the 6 µm microspheres occurred after 2 minutes of flow.

DIVI is only one example of a pathological or physiological process which can be investigated with the model. For example, atherosclerosis could be modeled in part using ECs, SMCs, and perhaps other cell types such as macrophages or foam cells. Virtually any other disease process which effects small to medium sized vessels could be investigated using this model.

The present invention has been described in terms of one or more preferred embodiments, and it should be appreciated that many equivalents, alternatives, variations, and modifications, aside from those expressly stated, are possible and within the scope of the invention.

What is claimed is:

1. A method of assaying an agent for its ability to cause drug-induced vascular injury, the steps comprising:
    (a) providing an in vitro blood vessel model including two elongated channels separated by a porous membrane coated on one side by an endothelial cell layer and coated on the other side by a smooth muscle cell layer, wherein the model is susceptible to the extravasation of red blood cells across the porous membrane due to drug-induced vascular injury, wherein one of the channels has a bottom formed by the porous membrane coated with the smooth muscle cell layer of the porous membrane; opposing sidewalls extending from the bottom; and a top that is open along a length of the channel;
    (b) flowing blood through the model;
    (c) passing the agent through the channel adjacent the endothelial cells; and
    (d) analyzing the channel adjacent to the smooth muscle cells for red blood cell extravasation, which indicates that the agent causes drug-induced vascular injury.

2. The method of claim 1, wherein the porous membrane has pore sizes ranging from approximately 0.1 to 30 µm and a porosity between approximately 5 and 50 percent.

3. The method of claim 1, wherein the porous membrane is a track-etched polycarbonate membrane.

4. The method of claim 1 wherein step a) further includes passing medium through the two channels at arterial flow rates.

5. A method of assaying an agent comprising the steps of:
    (a) providing an in vitro blood vessel model including two channels separated by a porous membrane coated on a first side with first cells and coated on a second side by second cells, wherein the model is susceptible to the extravasation of red blood cells across the porous membrane due to drug-induced vascular injury; wherein the model comprises:
        (i) a bottom layer defining a luminal channel;
        (ii) a top layer defining an open top smooth muscle channel so that when the open top smooth muscle channel contains a fluid, the fluid is exposed to air;
        (iii) a porous membrane sandwiched between the top layer and bottom layer to separate the channels, the porous membrane having a bottom side facing the luminal channel and being coated by an endothelial cell layer; and a top side facing the open top smooth muscle channel and being coated by a smooth muscle cell layer,
    wherein the porous membrane approximates an internal elastic lamina of blood vessels;
    (b) flowing blood through the model;
    (c) passing the agent through the channel adjacent the first cells; and
    (d) analyzing the channel adjacent to the second cells for red blood cell extravasation.

6. A method of assaying an agent comprising the steps of:
    (a) providing an in vitro blood vessel model including two channels separated by a porous membrane coated on a first side with first cells and coated on a second side by second cells, wherein the model is susceptible to the extravasation of red blood cells across the porous membrane due to drug-induced vascular injury; wherein the model comprises:
        (i) a bottom layer defining a luminal channel;
        (ii) a top layer defining a smooth muscle channel so that when the smooth muscle channel contains a fluid, the fluid is exposed to air, wherein a volume of the smooth muscle channel is relatively larger than a volume of the luminal channel;
        (iii) a porous membrane sandwiched between the top layer and bottom layer to separate the channels, the porous membrane having a bottom side facing the luminal channel and being coated by an endothelial cell layer and coated on a top side facing the smooth muscle channel by a smooth muscle cell layer, wherein the porous membrane approximates an internal elastic lamina of blood vessels;

wherein the smooth muscle channel has a bottom extending between opposing sidewalls and an open top;

(b) flowing blood through the model;
(c) passing the agent through the channel adjacent the first cells; and
(d) analyzing the channel adjacent to the second cells for red blood cell extravasation.

\* \* \* \* \*